(12) United States Patent  
Rondeau

(10) Patent No.: US 8,439,880 B2
(45) Date of Patent: May 14, 2013

(54) DRIP CHAMBER WITH FLOW CONTROL

(75) Inventor: Georges Rondeau, Braffe (BE)

(73) Assignees: Baxter Healthcare S.A., Glattpark (Opfikon) (CH); Baxter International Inc., Deerfield, IL (US)

( * ) Notice: Subject to any disclaimer, the term of this patent is extended or adjusted under 35 U.S.C. 154(b) by 288 days.

(21) Appl. No.: 12/954,375

(22) Filed: Nov. 24, 2010

(65) Prior Publication Data

US 2011/0125103 A1   May 26, 2011

Related U.S. Application Data

(60) Provisional application No. 61/264,376, filed on Nov. 25, 2009.

(51) Int. Cl.
*F16K 31/00* (2006.01)
*A61M 5/14* (2006.01)

(52) U.S. Cl.
USPC ........... 604/256; 604/251; 604/252; 604/253; 604/254; 604/255; 251/341

(58) Field of Classification Search .......... 604/251–255, 604/256, 246, 248, 31, 33, 247, 250, 249, 604/537, 99.01–99.04; 251/341, 343, 345, 251/347, 264, 266, 267, 268
See application file for complete search history.

(56) References Cited

U.S. PATENT DOCUMENTS

| | | |
|---|---|---|
| 2,032,305 A | 2/1936 | Poulin |
| 2,771,878 A | 11/1956 | Rolland et al. |
| 2,974,835 A | 3/1961 | Herbrick |
| 3,058,631 A | 10/1962 | De La Hitte |
| 3,664,339 A | 5/1972 | Santomieri |
| 3,850,346 A | 11/1974 | Richardson et al. |
| 3,868,973 A | 3/1975 | Bierman et al. |
| 3,880,401 A | 4/1975 | Wiltse |
| 4,043,332 A | 8/1977 | Metcalf |
| 4,230,300 A * | 10/1980 | Wiltse ........................ 251/205 |

(Continued)

FOREIGN PATENT DOCUMENTS

WO   WO-2007/041787 A1   4/2007

OTHER PUBLICATIONS

International Search Report and Written Opinion for corresponding International Application No. PCT/US2010/058080, dated May 9, 2011.

*Primary Examiner* — Bhisma Mehta
*Assistant Examiner* — Lauren M Peng
(74) *Attorney, Agent, or Firm* — Marshall, Gerstein & Borun LLP

(57) ABSTRACT

A flow control system includes a drip chamber having lower and upper wall sections and a collapsible wall extending between the lower and upper wall sections, a downwardly depending valve seat attached to the lower wall section, and a valve member disposed in the drip chamber, attached to the upper wall section and having a valve surface engageable with the valve seat. The system also includes a driver rotatably engaged to the lower and upper wall sections. Upon rotation of the driver in a first direction, the collapsible wall of the drip chamber moves between a collapsed condition in which the valve seat is sealingly engaged with the valve surface and an extended condition in which the valve seat is sufficiently spaced from the valve surface to form a flow passageway between the valve surface and the valve seat and permit flow through the opening of the drip chamber.

15 Claims, 12 Drawing Sheets

U.S. PATENT DOCUMENTS

| | | |
|---|---|---|
| 4,269,222 A | 5/1981 | Palti |
| 4,349,134 A | 9/1982 | Schuster et al. |
| 4,615,693 A | 10/1986 | Paradis et al. |
| 4,722,732 A | 2/1988 | Martin |
| 4,917,271 A | 4/1990 | Kanner et al. |
| 5,098,408 A | 3/1992 | Tarzian |
| 5,234,412 A | 8/1993 | Forberg |
| 5,360,412 A | 11/1994 | Nakao et al. |
| 5,415,641 A * | 5/1995 | Yerlikaya et al. ............. 604/251 |
| 5,655,689 A | 8/1997 | Fuchs et al. |
| 6,223,791 B1 | 5/2001 | Arsenault et al. |
| 6,354,346 B2 | 3/2002 | Arsenault et al. |
| 6,450,214 B1 | 9/2002 | Dyer et al. |
| 6,477,743 B1 | 11/2002 | Gross et al. |
| 6,571,994 B1 | 6/2003 | Adams et al. |
| 6,695,004 B1 | 2/2004 | Raybuck |
| 6,702,161 B2 | 3/2004 | Adams et al. |
| 6,997,437 B2 * | 2/2006 | Mitten .......................... 251/214 |
| 7,001,365 B2 | 2/2006 | Makkink |
| 7,261,226 B2 | 8/2007 | Adams et al. |
| 2005/0273062 A1 | 12/2005 | Franksson et al. |
| 2006/0178645 A1 * | 8/2006 | Peppel ........................... 604/249 |

* cited by examiner

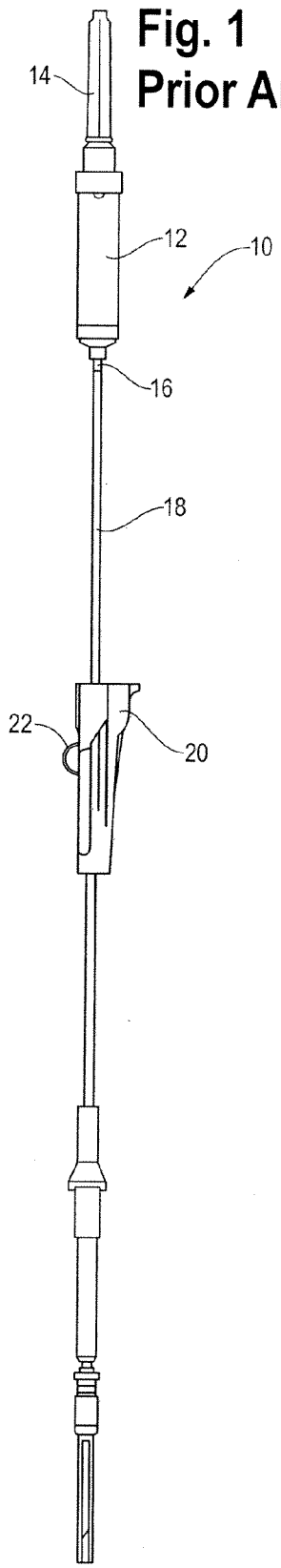
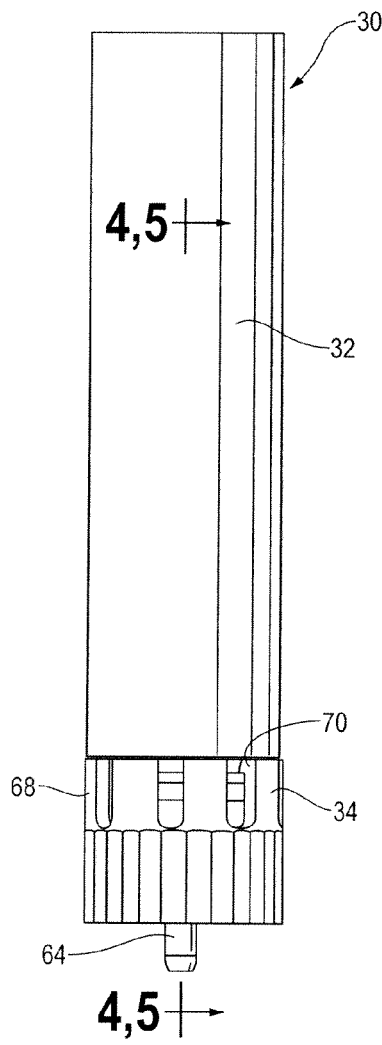
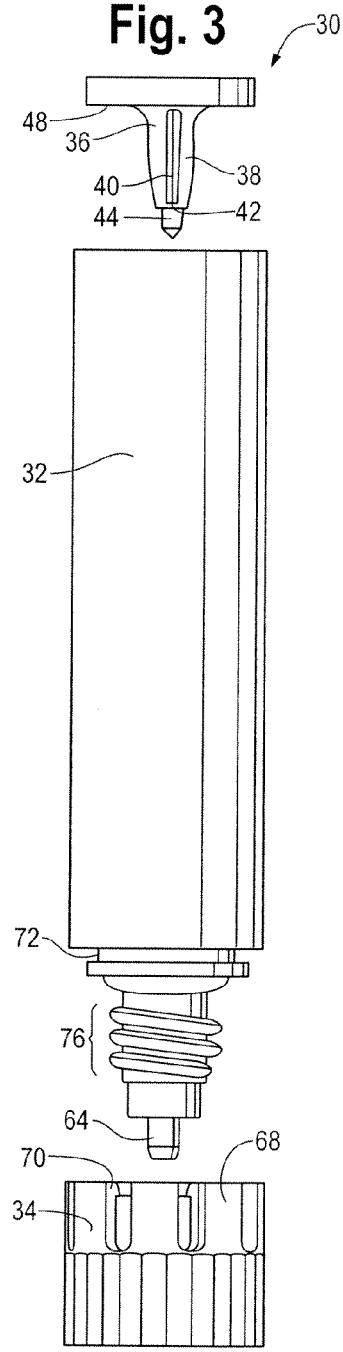

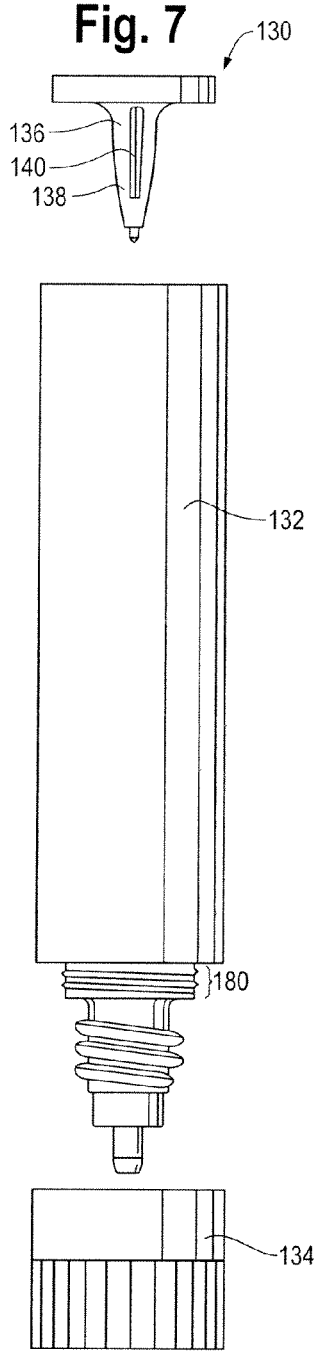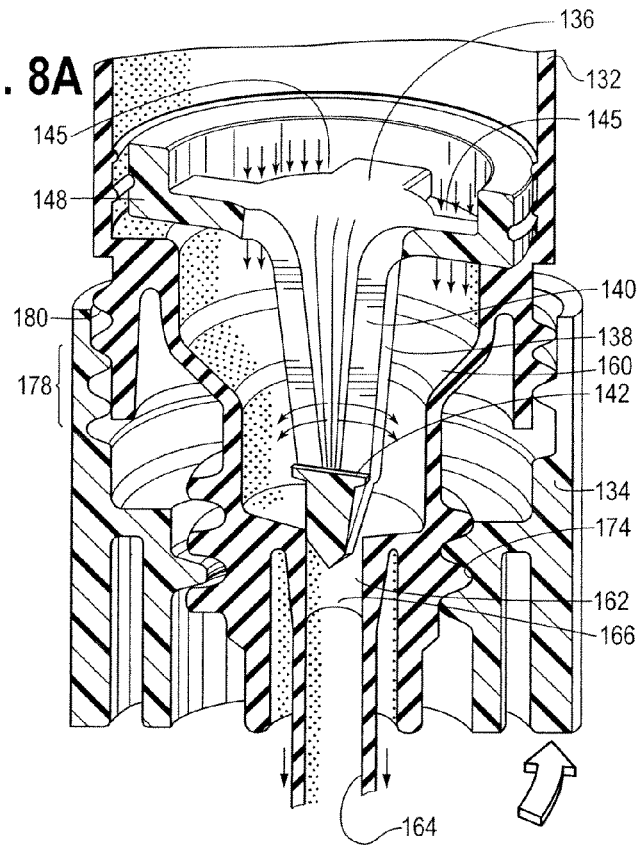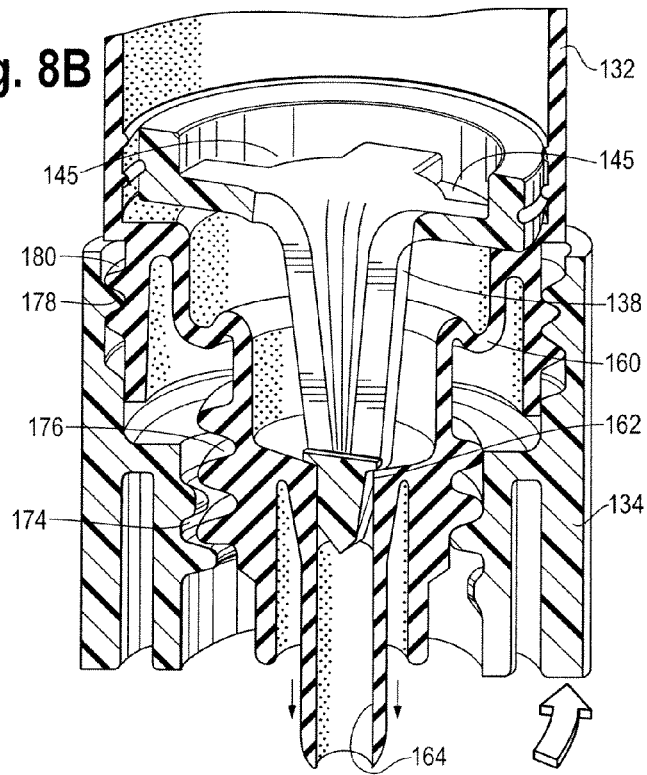

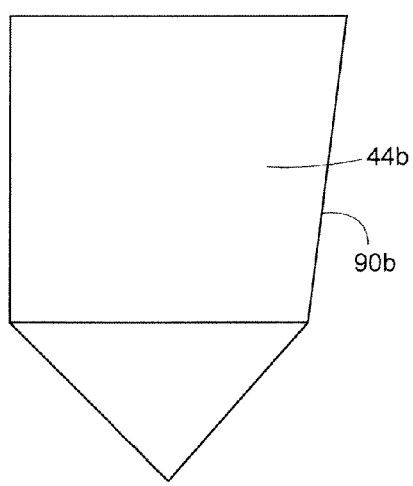
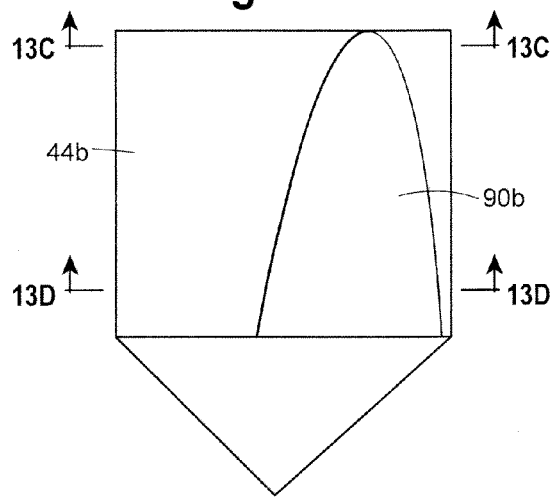
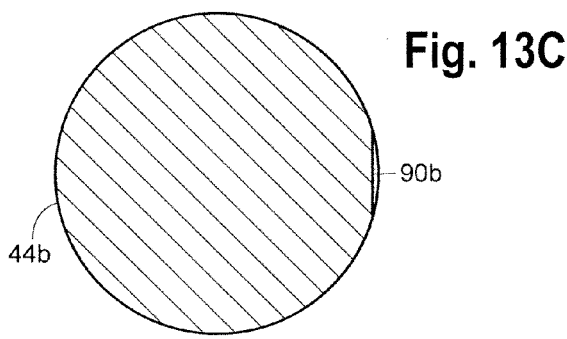
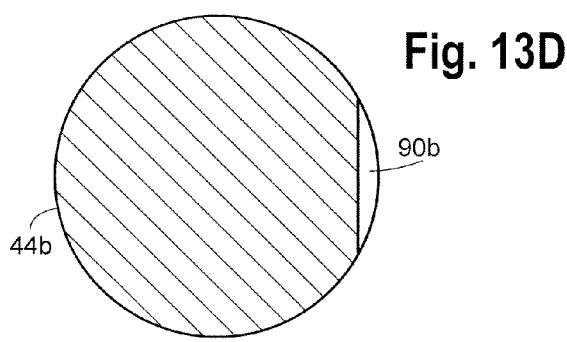

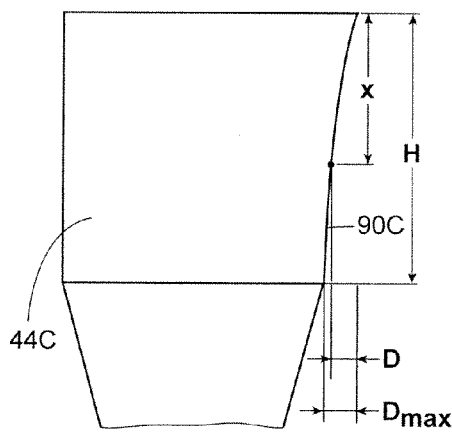
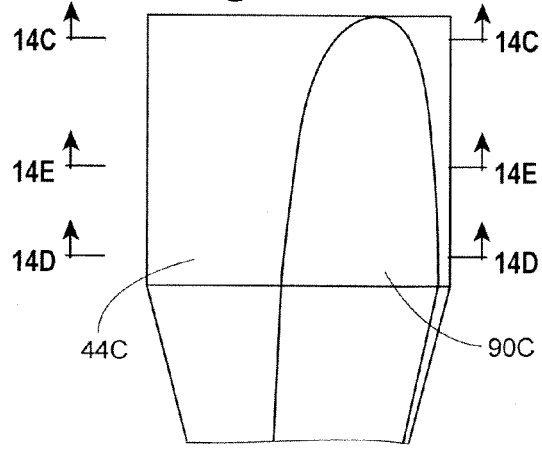
Fig. 14A
Fig. 14B
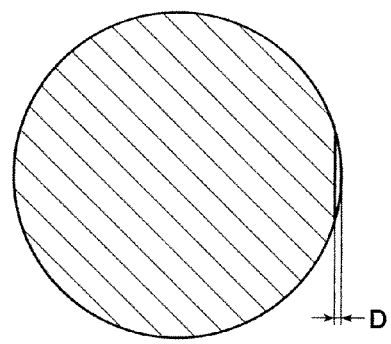
Fig. 14C
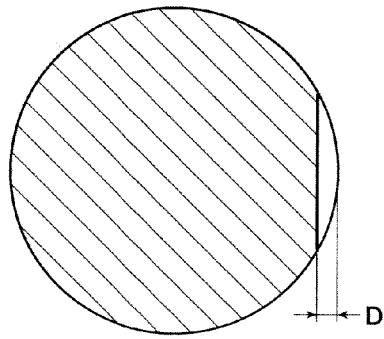
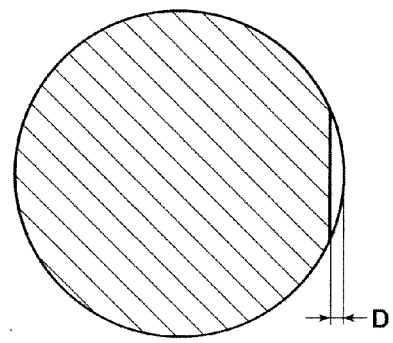
Fig. 14D
Fig. 14E

DRIP CHAMBER WITH FLOW CONTROL

REFERENCE TO RELATED APPLICATIONS

This application claims the benefit of U.S. Application No. 61/264,376, filed Nov. 25, 2009, which is hereby incorporated by reference in its entirety herein.

FIELD OF THE DISCLOSURE

This disclosure relates generally to systems for regulating the flow of fluid through a fluid set into a patient and, more specifically, to devices for achieving precise control over a range of flow rates of fluids delivered in perfusion, transfusion, and infusion systems.

BACKGROUND

Many conventional flow control systems for perfusion, transfusion, and infusion systems are provided by the use of a flow regulator in the form of a roller clamp attached to tubing leading from a drip chamber to the patient. Such roller clamps rely on deformation of the tubing to modify the fluid flow path in order to slow down or speed up the rate of flow to the patient. Over time, the stress induced in the tubing and creep effects gradually alter the resiliency and dimensions of the tubing, altering the flow rate as set by the health care provider using the roller clamp.

The effects of stress and creep are particularly profound when non-PVC tubing is used, such that roller clamps may be almost non-effective when used with non-PVC tubing. While PVC tubing is more resistant to such degradation and performs better with roller clamps than non-PVC tubing, some alteration is still present and thus a flow control system that does not allow unintended alteration of the flow rate through the tubing of perfusion, transfusion or infusion systems would be preferable.

Another drawback of using roller clamps is the difficulty in setting the flow rate of a liquid limited patient such as a neonatal patient. For such a patient, the ability to accurately set a low flow rate is very important. The tubing clamp is ill-suited for such setting as even a slight movement of the roller can lead to a more than desired change in the flow rate thereby leading to multiple slight movements of the roller to set such a rate. This prolongs the time needed to set the rate. In addition, even a slight creep over time caused by the roller clamp can result in a change in the flow rate bringing it outside the desired range. This leads to the necessity for the health care provider to frequently check and if needed adjust the flow rate back to the desired rate.

A further drawback of conventional flow control systems is the possibility of providing a closed loop fluid control to the flow control system. Roller clamps are configured to be manipulated by the health care provider and are problematic to incorporate into an automatic system which may manipulate the clamp in dependence on sensed parameters such as the monitored flow or condition of the patient.

SUMMARY

According to an aspect of the present disclosure, a flow control system includes a drip chamber having a lower wall section, an upper wall section and a collapsible wall extending between the lower wall section and the upper wall section, a downwardly depending valve seat attached to the lower wall section, the drip chamber forming a downstream opening in fluid communication with the valve seat, and a valve member disposed in the drip chamber and attached to the upper wall section and having a valve surface engageable with the valve seat. The system also includes a driver rotatably engaged to the upper wall section and lower wall section. Upon rotation of the driver in a first direction, the collapsible wall of the drip chamber moves between a collapsed condition in which the valve seat is sealingly engaged with the valve surface and an extended condition in which the valve seat is sufficiently spaced from the valve surface to form a flow passageway between the valve surface and the valve seat and permit flow through the opening of the drip chamber.

According to another aspect of the present disclosure, a method for regulating the flow of fluid through a drip chamber includes rotating a driver that is in rotatable engagement with an upper wall section and a lower wall section of a drip chamber relative to the drip chamber to move a collapsible wall that extends between the upper and lower wall sections. The collapsible wall moves between a collapsed condition in which an associated valve seat is sealingly engaged with a valve surface, and an extended condition in which the valve seat sufficiently spaced from the valve surface to form a flow passageway between the valve surface and the valve seat to permit flow therethrough.

BRIEF DESCRIPTION OF THE SEVERAL VIEWS OF THE DRAWINGS

FIG. 1 is a plan view of a prior art drip chamber and flow regulator in the form of a roller clamp attached to tubing leading from a drip chamber;

FIG. 2 is a plan view of a flow control system of a first embodiment of the present disclosure;

FIG. 3 is an exploded plan view of the flow control system illustrated in FIG. 2;

FIG. 7 is an exploded plan view of a second embodiment of a flow control system of the present disclosure;

FIG. 8A is a perspective cross-sectional view of the flow control system of FIG. 7, illustrating a collapsible wall of the flow control system in an extended condition, with a valve seat of the drip chamber drawn downward and away from a generally cylindrical valve surface of a valve member secured within the drip chamber, permitting fluid flow through windows between joints attaching the conical valve stem of the valve member to a flange of the valve member, and permitting drainage of an interior of the conical region through one or more elongate slits provided along the hollow valve stem of the valve member, with a directional arrow indicating rotation of the driver in a direction that decreases and ultimately stops flow through the drip chamber, which generally cylindrical valve surface may include an angled planar groove along one side of a mating surface thereof;

FIG. 8B is a perspective cross-sectional view similar to FIG. 8A, illustrating the collapsible wall of the drip chamber in a contracted condition;

FIG. 13A is a front plan view of a generally cylindrical valve surface of a valve member for use in a drip chamber of the present disclosure, such as the valve member illustrated in FIGS. 4, 7, 8A, 8B, 9A and 9B, including an angled planar groove along one side of a mating surface of the generally cylindrical valve surface;

FIG. 13B is a side plan view of the generally cylindrical valve surface of the valve member illustrated in FIG. 13A;

FIG. 13C is a cross-sectional view taken along lines 13C-13C of FIG. 13B;

FIG. 13D is a cross-sectional view taken along lines 13D-13D of FIG. 13B;

FIG. 14A is a front plan view of a generally cylindrical valve surface of a valve member for use in a drip chamber of the present disclosure, including parabolic-shaped groove along one side of a mating surface of the generally cylindrical valve surface;

FIG. 14B is a side plan view of the generally cylindrical valve surface of the valve member illustrated in FIG. 14A;

FIG. 14C is a cross-sectional view taken along lines 14C-14C of FIG. 14B;

FIG. 14D is a cross-sectional view taken along lines 14D-14D of FIG. 14B;

FIG. 14E is a cross-sectional view taken along lines 14E-14E of FIG. 14B;

DETAILED DESCRIPTION OF THE PREFERRED EMBODIMENTS

Introductory Remarks

Figure 4:
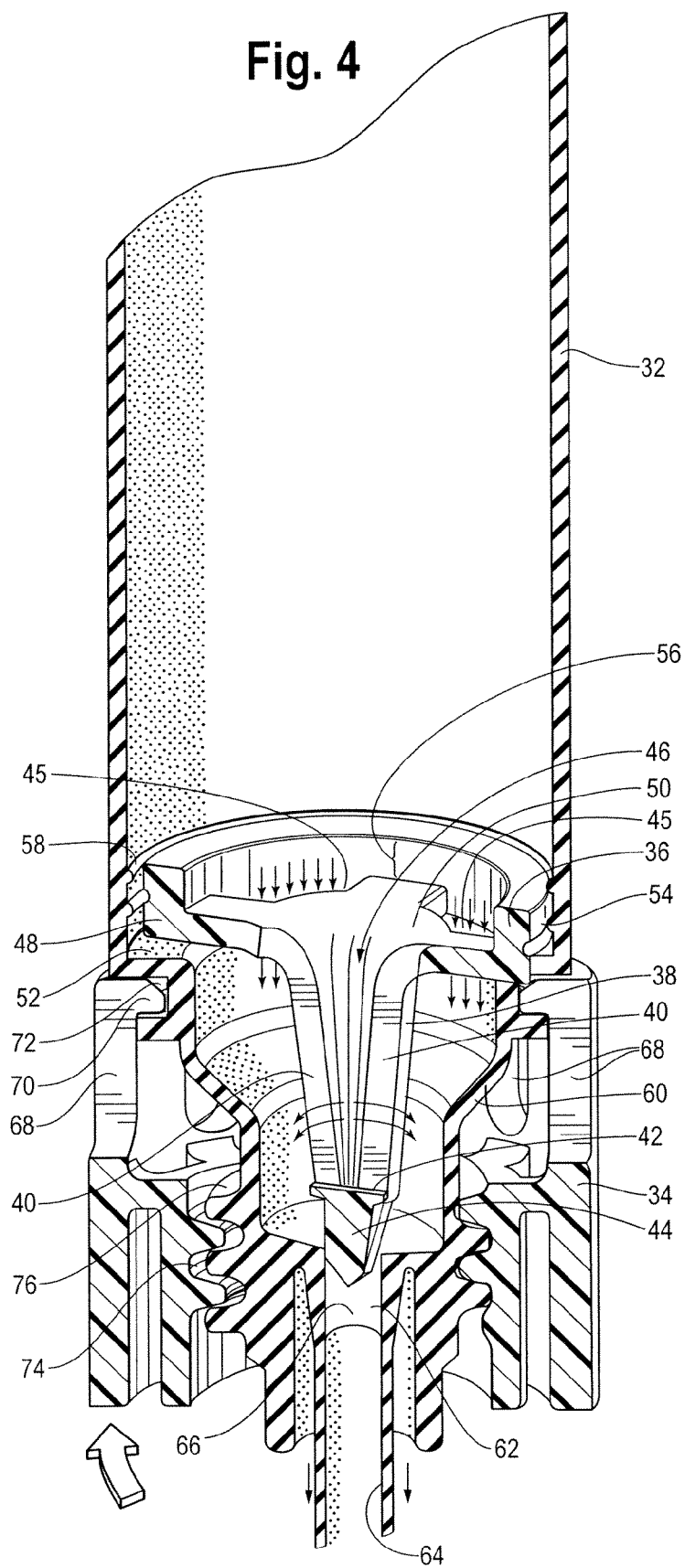
FIG. 4 is a perspective cross-sectional view, taken along lines 4-4 of FIG. 2, illustrating a collapsible wall of a drip chamber of the flow control system moving toward a fully-extended condition, with a valve seat of the drip chamber drawn downward and away from a generally cylindrical valve surface of a valve member secured within the drip chamber, as a result of rotation of a driver in a counter-clockwise direction (from a perspective below the driver, looking upward), permitting fluid flow primarily through windows between joints attaching the conical valve stem of the valve member to a flange of the valve member, and permitting drainage of an interior of the conical region through one or more elongate slits provided along the hollow valve stem of the valve member, which generally cylindrical valve surface may include an angled planar groove along one side of a mating surface thereof.

In an illustrated embodiment of the present disclosure, a fluid flow control system is provided that includes a drip chamber having a radially-inwardly-directed annular ledge in which a conical-shaped valve member is securely seated, with a conical valve stem of the valve member pointing downstream. The interior of the drip chamber further includes a region depending downstream from the annular ledge, with an axially-extending opening at a downstream end of the drip chamber and a collapsible wall extending between the opening and the annular ledge. The downstream region forms a valve seat within the drip chamber that is shaped complementary to a valve surface, such as a generally cylindrical valve surface, of the valve member. As used herein, the term "generally cylindrical" would be understood by a person of ordinary skill in the art to mean either perfectly cylindrical, i.e. with a circumferential sidewall that is perpendicular relative to a horizontal plane passing through the valve member, as well as tapered or slanted to a degree sufficient to facilitate removal of the valve member from an injection molding cavity, such as 1°. As explained in greater detail below, a tapered conical shape may also be considered as one of several types of grooves along the generally cylindrical valve surface that result in better control over flow rates through the drip chamber. A rotating driver is configured to operationally engage the drip chamber to move the valve seat in an axial direction relative to the generally cylindrical valve surface of the valve member.

The upstream end of the drip chamber serves as an inlet for fluid. The upstream end of the drip chamber may be provided with a spike (which may be bonded thereto) to pierce and bring the drip chamber into fluid communication with a fluid source, such as a flexible container of fluid. Alternatively, the upstream end of the drip chamber may be enclosed and bonded to a tube that fluidly connects a separate spike with an opening in the drip chamber to place the interior of the drip chamber into fluid communication with the interior of the spike and the tube.

The conical valve stem of the valve member is attached to a flange that sits on the radially-inwardly-directed annular ledge of the drip chamber. A plurality of openings or windows is provided between arms or joints connecting the conical valve stem of the valve member to the flange. The conical valve stem includes at least one opening, preferably in the form of an elongate slit extending along the wall thereof.

When the collapsible wall is in a collapsed condition, the valve seat contacts the generally cylindrical valve surface of the valve member below a lower end of the slit, thereby preventing any flow of fluid downstream between the exterior of the conical valve stem of the valve member and the valve seat. As the collapsible wall is extended, the valve seat is gradually moved in an axial direction away from the generally cylindrical valve surface of the valve member, thereby opening a fluid path between the valve surface and the valve seat and increasing the rate of fluid flow to the axially-extending opening at the downstream end of the drip chamber.

It is found that by providing a groove in at least a portion of the generally cylindrical valve surface at a mating surface of that valve surface, there is an enhanced ability to regulate flow through the drip chamber of the present disclosure. The groove may take the form of a planar cut along one side of the generally cylindrical valve surface. Alternately, the groove may take the form of a curved or parabolic cut along one side of the generally cylindrical valve surface. As a further alternative, the groove may take the form of a rotated arcuate channel along one side of the generally cylindrical valve surface. As yet a further alternative, the groove may effectively take the form of a taper around the circumference of the generally cylindrical valve surface, such that a generally conical shape is imparted to the valve surface which a generally cylindrical shape is maintained by the valve seat. By altering the shape and dimensions of the groove in the generally cylindrical valve surface, a variety of flow patterns may be achieved. A high resolution of flow control for small volumes of liquid is particularly desirable for delivery of small doses of fluids to patients on tight flow restrictions, such as neonatal patients.

The main flow paths from the portion of the drip chamber above the valve member to the axially-extending opening at the downstream end of the drip chamber are provided by the windows located between the joints connecting the valve stem of the valve member to the flange seated on the annular ledge of the drip chamber. The elongate slit extending along the wall of the valve member facilitates drainage of the interior of the conical region of the needle member, thereby avoiding waste of fluid.

The collapsible wall is actuated between its collapsed and extended conditions via the driver having an upper end that is secured to an exterior of the drip chamber in a manner that is rotatable, but axially fixed, relative to the portion of the drip chamber above the collapsible wall. The driver includes an internally threaded wall that engages an externally threaded region disposed below the collapsible wall and extending radially outwardly of the valve seat of the drip chamber. Rotation of the driver in a first direction imparts axial movement to the collapsible wall relative to the generally cylindrical valve surface of the conical fluid control needle member, drawing the valve seat away from the generally cylindrical valve surface of the valve member and permitting or increasing fluid flow between the valve member and the valve seat, and thus through the opening at the downstream end of the drip chamber. Depending on the shape and dimensions of the groove in the mating surface of the valve surface, the flow down to the lower region of the drip chamber may be restricted to the groove during at least an initial portion of axial travel of the valve seat away from the generally cylindrical valve surface of the valve member. Rotation of the driver in a second, opposite direction reverses the axial movement of the collapsible wall relative to the conical fluid control needle member, bringing the valve seat up toward the generally cylindrical valve surface of the valve member and slowing or stopping fluid flow between the valve member and the valve seat. If desired, the rotation of the screw may be calibrated so as to achieve predictable control over the rate of fluid flow from the drip chamber. The calibration is not necessarily linear, inasmuch as, depending upon such variables as the location(s), shape, and dimensions of the groove, there may be greater resolution as to adjustments in flow rate along an initial axial portion of the range of movement between the valve seat and the generally cylindrical valve surface of the valve member.

According to a second illustrated embodiment, the driver is provided with an upper internally threaded region of a first pitch along a portion that engages an externally threaded region of a drip chamber at a location above the collapsible wall, and a lower internally threaded region of a second pitch that engages an externally threaded region of the collapsible wall of the drip chamber. As in the first embodiment, a conical flow control needle having an opening, preferably in the form of an elongate slit, is provided along the conical region thereof. The driver of this second embodiment is rotatable relative to the drip chamber, but unlike the first embodiment, is displaced axially relative to the portion of the drip chamber above the collapsible wall due to engagement of the upper internally threaded region of the driver with the externally threaded region of the drip chamber above the collapsible wall.

The first pitch of the upper internally threaded region of the driver and the mating externally threaded region of the drip chamber at a location above the collapsible wall is less than the second pitch of the lower internally threaded region of the driver and the externally threaded region of the collapsible wall of the drip chamber. This difference in pitch effects relative axial movement between the region of the drip chamber below the collapsible wall and the region of the drip chamber above the collapsible wall upon rotation of the driver. As a result of this difference in relative axial movement, as in the first embodiment, rotation of the driver in a first direction imparts axial movement to the collapsible wall relative to the generally cylindrical valve surface of the conical fluid control needle member, drawing the valve seat downward and away from the generally cylindrical valve surface of the valve member and permitting or increasing fluid flow between the generally cylindrical valve surface of the conical flow control needle and the valve seat, and thus through the opening at the lowermost end of the drip chamber. Rotation of the driver in a second, opposite direction reverses the axial movement of the collapsible wall relative to the generally cylindrical valve surface of the conical fluid control needle member, bringing the valve seat up toward the top of the generally cylindrical valve surface of the valve member and slowing or stopping fluid flow between the valve member and the valve seat.

Embodiments

A conventional flow control system 10 for use in perfusion, transfusion or infusion applications is illustrated in FIG. 1. The flow control system 10 includes a drip chamber 12 having a spiked inlet or upstream end 14 and an outlet or downstream end 16, a length of tubing 18 extending from the outlet 16 of the drip chamber 12, and a roller clamp 20 provided along the length of the tubing 18, downstream of the outlet 16 of the drip chamber 12. The roller clamp 20 includes a roller 22 that pinchingly deforms the tubing 18 to alter the flow rate of fluid through the tubing 18.

As discussed in the Background section, the precision of such devices is directly dependent upon intensive monitoring of the system over time by the health care provider. Further, over time the roller 22 may induce stresses and creep effects in the tubing, causing fatigue or otherwise degrading the tubing, diminishing the precision and effectiveness of the roller clamp 20 in controlling flow rate through the tubing 18 or requiring additional monitoring In addition, such conventional flow control systems generally do not permit variation in accordance with the particular needs of the individual patient; that is, the same tubing-and-roller-clamp system may be used with an adult receiving a therapy with a wide treatment range or with an infant receiving a therapy that must be kept within a narrow treatment range.

Turning to FIGS. 2-5, a first embodiment of a flow control system 30 is provided with a drip chamber 32, a driver 34, and a valve member 36 that is securely received within the drip chamber 32 toward a lower end of the drip chamber 32, and does not move relative to the drip chamber 32. The drip chamber 32 may be made of SEBS (styrene-ethylene-butylene-styrene) so as to permit a degree of flexibility, while the driver 34 and the valve member 36 may be made of ABS (acrylonitrile butadiene styrene) so as to provide a greater degree of rigidity. For reasons elaborated upon below, the system 30 according to certain embodiments is made of such non-PVC materials, as it may be desired to attach the system 30 to tubing that is also made of non-PVC materials (such as EVA (ethylene vinyl acetate) or polyurethane) by press fitting, bonding or some other attachment mechanism to form a completely non-PVC set according to certain embodiments. The system 30 (along with such other portions of an associated set as may be attached) may be sterilized using ethylene oxide (ETO) sterilization techniques, although it may also be sterilized by gamma or e-beam sterilization techniques.

Although not shown, the upper end of the drip chamber 32 may be provided with an integral spike (which may also be made of ABS) to puncture an infusion bag or other fluid source to introduce fluid from the fluid source into the drip chamber 32 of the flow control system 30. Alternately, the upper end of the drip chamber 32 may be enclosed, but provided with a port or opening to which a spiked tube is bonded or otherwise connected. In any event, the drip chamber 32 will typically include a drop former (such as in the form of a tube of a certain length disposed in a cap) at the upper end, which drop former is in fluid communication with the spike and forms drops within the drip chamber 32, as is conventionally known.

As illustrated, the valve member 36 includes a conical valve stem 38 with at least one opening. As also illustrated, the valve stem 38 is hollow, and the at least one opening is preferably in the form of one or more slits 40 extending along a side of the conical stem 38, the fluid-receiving interior 46 of the stem 38 providing a staging area for fluid to pass through the slits 40. The slits 40 terminate at a lower end 42 above a valve surface 44 of the valve member 36. The slits 40 may limit fluid retention region below the lower end 42 of the slit 40 of the valve member 36, so as to avoid unwanted fluid retention within the valve member 36. While a particular shape has been illustrated for the stem 38, it will be recognized that the valve stem 38 may alternatively be solid instead of hollow (although a hollow form may facilitate molding), and need not have the conical shape shown.

A radially outwardly-projecting flange or ring 48 is provided at an upper end 50 of the stem 38, which flange or ring 48 is seated on an upper surface formed by radially inwardly-projecting ledge 52 in the drip chamber 32. The stem 38 may be connected to the flange or ring 48 by a plurality of arms or joints, defining windows 45 therebetween, the windows 45 providing a main flow path between a portion of the drip chamber 32 above the valve member 36 and a portion of the drip chamber 32 below the valve member 36 and facilitating priming of the chamber 32 thereby. While one or the other of the slits 40 and the windows 45 may be omitted, according to certain embodiments, such as the illustrated embodiment, both may be provided. An annular wall 54 extends upwardly from the radially outwardly-projecting flange or ring 48, and may define a filter receiving area 56 within the valve member 36 that can receive a filter (not shown).

To prevent movement relative to the drip chamber 32, the valve member 36 may be secured within the drip chamber 32 with an interference or friction fit. Alternately or in addition, an annular securement rib 58 or radially-inwardly directed nubs or locking tabs (not shown) may be provided on the inner wall of the drip chamber 32, spaced a distance above the radially inwardly-projecting ledge 52 slightly greater than the combined height of the radially outwardly-projecting flange 48 and annular wall 54. When the valve member 36 is pushed down into the drip chamber 32, past the annular securement rib 58, nubs, or locking tabs, the valve member 36 is secured in place within the drip chamber 32, even if there is not an interference or friction fit between the inner wall of the drip chamber 32 and the annular wall 54 of the valve member 36.

The drip chamber 32 includes a collapsible wall 60 (which according to the illustrated embodiment may be a bellows-type wall) that depends downwardly from the radially inwardly-projecting ledge of an interior wall of the drip chamber 12 and may taper radially inwardly from top to bottom, as illustrated. Stated slightly differently, the collapsible wall 60 extends between an upper wall section and a lower wall section. A valve seat 62 is attached to (and according to certain embodiments, integrally attached (i.e., formed as a single piece)) and depends downwardly from a bottom end of the collapsible wall 60 (e.g., from the lower wall section). The valve seat 62 is complementary to the valve surface 44 of the valve member 36, or at least to a portion of the valve member 36 below the lower end 42 of the slit 40. The valve seat 62 is in fluid communication with and terminates at an axially-extending opening 64 at a lowermost downstream end 66 of the drip chamber 32. Tubing (not shown) may be attached to an exterior of the axially-extending opening 64 to deliver fluid from the drip chamber 32 to a patient.

Figure 5:
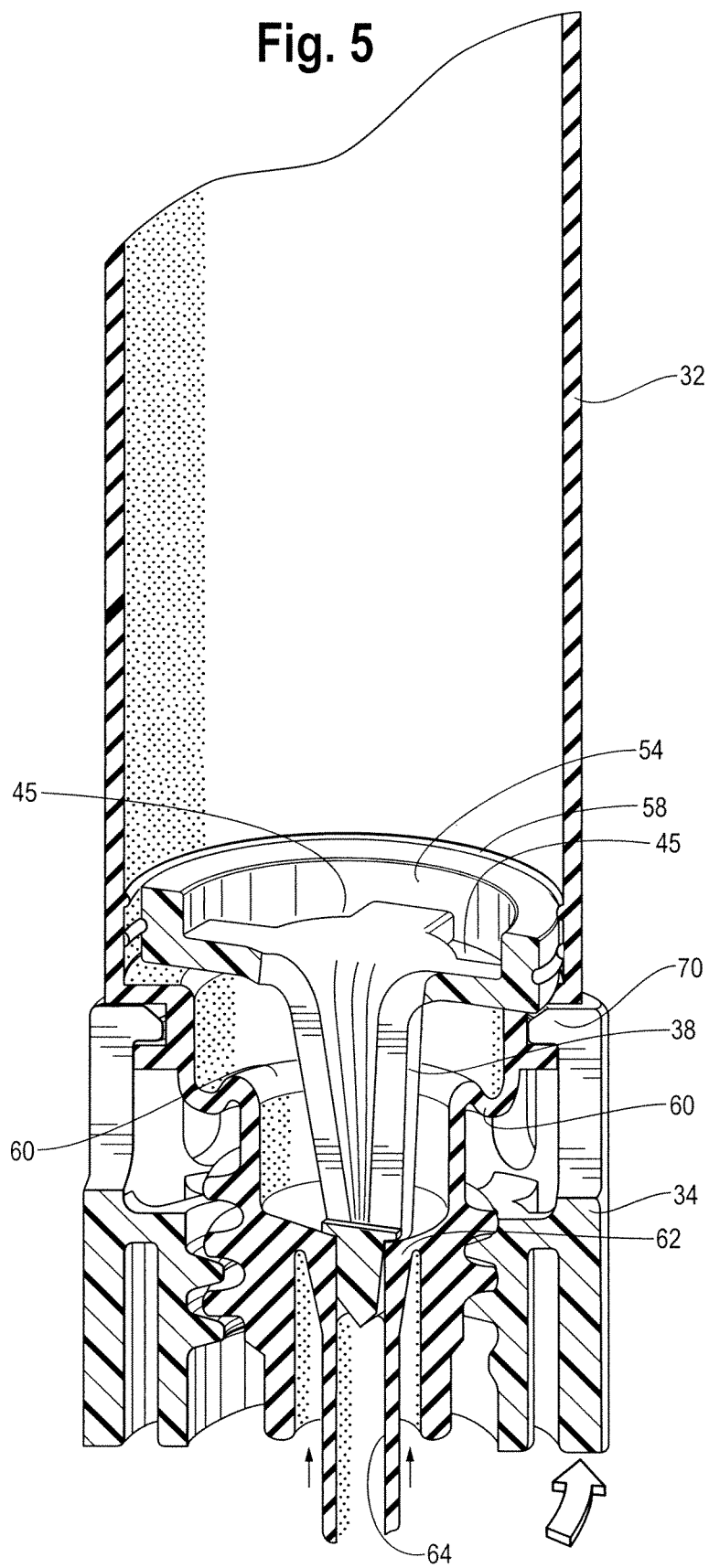
FIG. 5 is a perspective cross-sectional view similar to FIG. 4, taken along lines 5-5 of FIG. 2, illustrating the collapsible wall of the drip chamber moving into a fully collapsed condition, as a result of rotation of the driver in a clockwise direction (from a perspective below the driver, looking upward)

The collapsible wall 60 is actuatable between an extended condition, as illustrated in FIG. 4, and a collapsed condition, as illustrated in FIG. 5. When the collapsible wall 60 is the collapsed condition, the valve seat 62 (which may be attached to the upper wall section referred to above) sealingly engages the valve surface 44, preventing any flow of fluid from the drip chamber 32 to the patient. Moving the collapsible wall 60 toward its extended condition gradually moves the valve seat 62 in an axial direction downward, away from the valve surface 44. This separation of the valve seat 62 from the valve surface 44 opens a fluid path between the valve member 36 (and in particular the valve surface 44) and the valve seat 62, permitting or increasing the rate of fluid flow through the axially-extending opening 64 of the drip chamber 32. The width of a separation or gap formed between the valve seat 62 and the valve surface 44 forms a flow path which may thus be varied to operationally control the rate of the flow of fluid through the drip chamber 32.

According to this first embodiment, the valve seat 62 is actuated by the driver 34, which may be in the form of a collar or ring disposed about a lower end of the drip chamber 32, although it is not a requirement that the driver completely encircle the lower end of the drip chamber 32 according to all embodiments. The driver 34 includes a plurality of snap fit projections 68 in the form of arcuate walls, each with a radially inwardly-directed rib 70 thereon. The radially inwardly-directed ribs 70 are disposed into a recessed annular ring or groove 72 in an exterior wall of the drip chamber 32 to rotatably engage the driver 34 with the drip chamber 32, and in particular the upper wall section. The groove 72 is disposed above the collapsible wall 60. The driver 34 further includes an internally threaded region 74. The drip chamber 32 includes an externally threaded lower wall section 76 disposed below the collapsible wall 60, and extending radially outward of the valve seat 62 as illustrated. The threaded sections 74, 76 rotatably engage the driver 34 with the lower wall section of the drip chamber 32. Each of the snap fit projections 68 extends upward from the internally threaded region 74 of the driver 34. In the illustrated embodiment, the driver 34 includes a counter-clockwise thread, such that a rotation of the driver 34 in a clockwise direction will decrease, and ultimately stop, the flow.

The driver 34 is rotatable relative to the drip chamber 32, but the snap fit projections 68 maintain the driver 34 and the portion of the drip chamber 32 above the collapsible wall 60 in a constant relative axial position. Rotation of the driver 34 in a first direction (such as a clockwise direction, from a perspective below the driver 34, looking upward, as indicated by the curved arrow in FIG. 5) urges the collapsible wall 60, with which the externally threaded lower wall section 76 is in communication, toward its collapsed condition, decreasing the gap between the valve seat 62 and the valve surface 44, and ultimately occluding the flow through the drip chamber 32 (indicated by the upward-pointing arrows in FIG. 5). Rotation of the driver 34 in a second direction (such as a counter-clockwise direction, from a perspective below the driver 34, looking upward, indicated by the curved arrow in FIG. 4), opposite to the first direction, urges the collapsible wall 60 toward its extended condition, increasing the gap or space between the valve seat 62 and the valve surface 44, and thereby widening the flow path between the valve member 36 and the valve seat 62 and permitting flow through the opening of the drip chamber 32.

The displacement of the valve seat 62 upon rotation of the driver 34 a given amount is a function of the pitch of the threads of the internally threaded region 74 of the driver 34 and the externally threaded lower wall section 76 of the drip chamber 32, as well as a function of the direction of the threads (i.e. counter-clockwise). However, given the rigid nature of the driver 34, it is believed that the displacement of the valve seat 62 relative to a given movement of the driver 34 shall remain relatively fixed over the operational life of the drip chamber 32. As a consequence, it is further believed that the operation of the drip chamber 32 in accordance to movement of the driver 34 is relatively stable and predictable, as compared with the tubing-and-roller-clamp system described above, which may become both less stable and less predictable over time, requiring a greater time investment when fine control is desired because the degree of resolution may vary.

Figure 6:
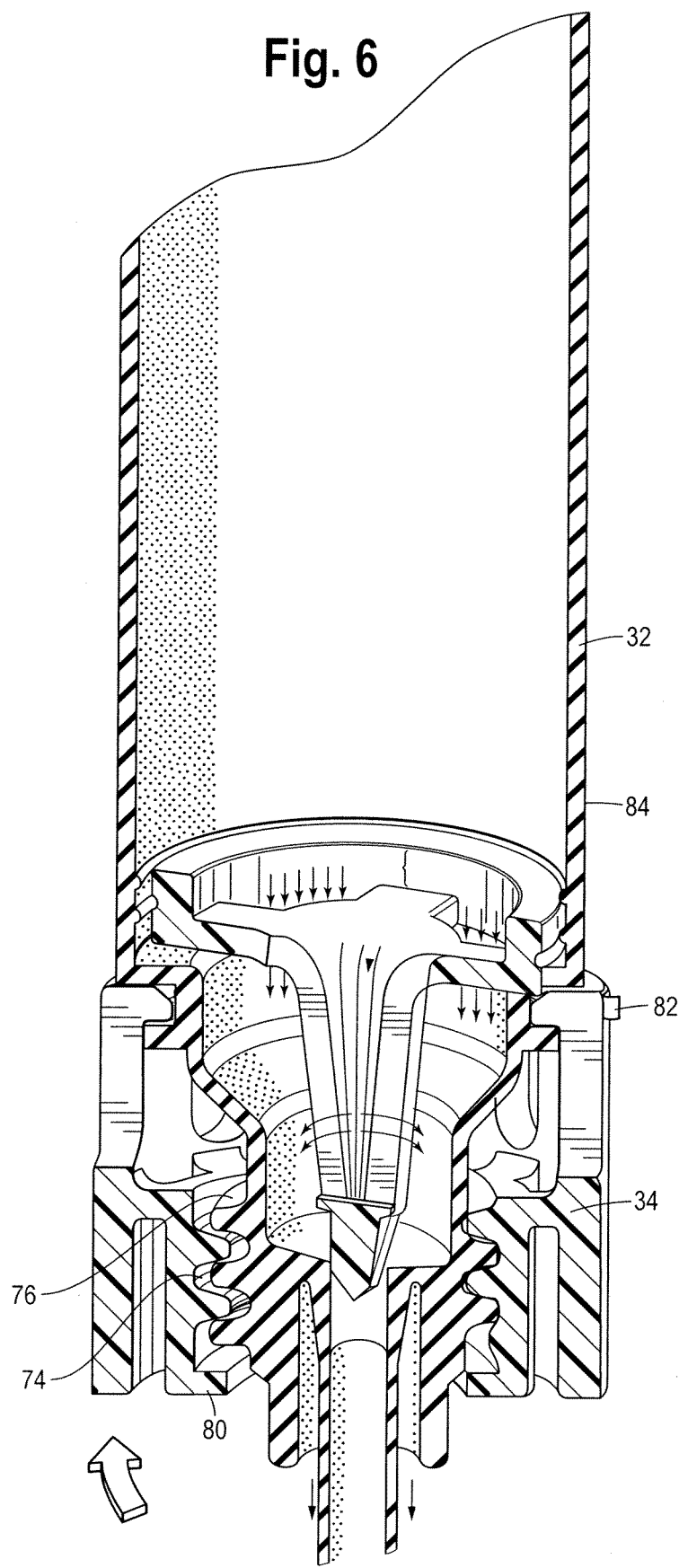
FIG. 6 is a perspective cross-sectional view of a variant of the embodiment illustrated in FIGS. 2-5, including features for identifying the extent of rotation of the driver relative to the drip chamber.
Figure 9A:
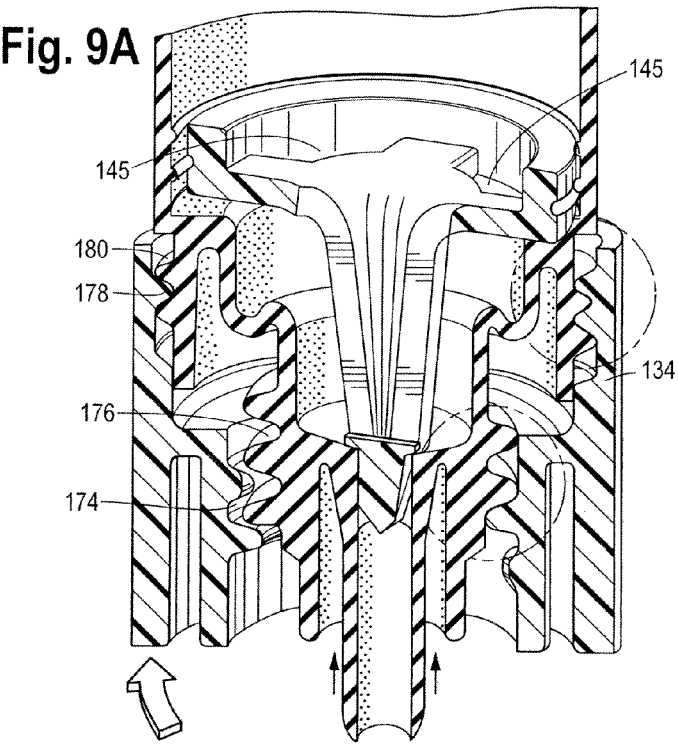
FIG. 9A is a perspective cross-sectional view similar to FIG. 8B, but with a directional arrow indicating rotation of the driver in a direction that initiates or increases the rate of flow through the drip chamber.
Figure 10:
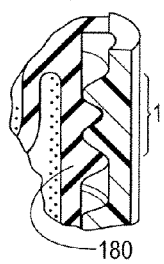
FIG. 10 is an enlarged cross-sectional view of the upper internally threaded region of the driver and mating externally threaded region of the drip chamber at a location above the collapsible wall of the flow control system of FIG. 7, taken along line 9 of FIG. 9A.
Figure 11:
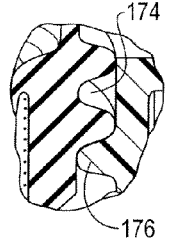
FIG. 11 is an enlarged cross-sectional view of the lower internally threaded region of the driver and mating externally threaded region of the collapsible wall of the drip chamber of the flow control system of FIG. 7, taken along line 11 of FIG. 9A.
Figure 9B:
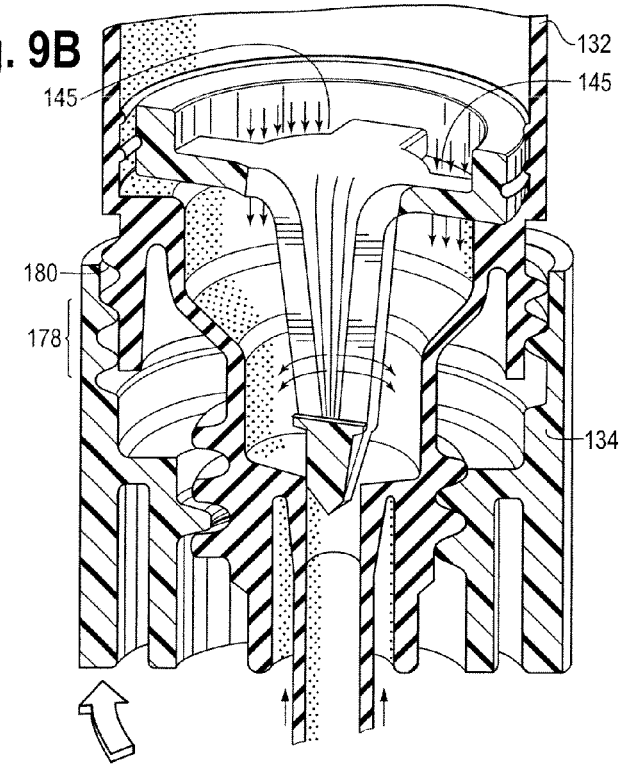
FIG. 9B is a perspective cross-sectional view similar to FIG. 8A.

FIG. 6 illustrates a variant of the embodiment illustrated in FIGS. 2-5. According to this variant, the driver 34 includes an inwardly radially depending flange or rim 80. The rim 80 is designed to interfere with the threads 76 on the drip chamber 32 to limit the motion of the drip chamber 32 in the downward axial direction. When the threads 76 contact the rim 80 for example, the user is provided with a tactile indication that the drip chamber 32 has achieved its extrememost position in the downward direction. The abutment of the threads 76 (or some other portion of the drip chamber 32) with the rim 80 may also prevent overextension of the collapsible wall 60 that may otherwise damage the wall 60. In addition, the variant includes an indicator tab 82 which may be used in conjunction with markings or indicia applied to an exterior surface 84 of the drip chamber 32 to permit a visual indication of the movement (rotation) of the driver 34 relative to the drip chamber 32, which visual indication may permit the user to more quickly achieve a desired flow rate through the system.

It will be recognized that embodiment of the driver 34 illustrated in FIGS. 2-5 is simply one example of a driver for use in the disclosed fluid control system, as it relates to the mounting of the driver to the drip chamber, for example. Turning then to FIGS. 7-11, a second embodiment of a flow control system 130 of the present disclosure is illustrated therein. Like the first embodiment, the flow control system 130 of the second embodiment includes a drip chamber 132, a driver 134, and a valve member 136 having a hollow conical stem 138 including at least one opening, preferably in the form of a slit 140 and windows 145 defined by a plurality of arms or joints by which the conical stem 138 is connected to an annular lip or ring 148. The windows 145 provide a main flow path between a portion of the drip chamber 132 above the valve member 136 and a portion of the drip chamber 132 below the valve member 136. The driver 134 includes an upper internally threaded region 178 (which may be of a first pitch) along a portion that engages an upper externally threaded region 180 of the drip chamber 132 at a location above a collapsible wall 160 of the drip chamber 132. The driver 134 further includes a lower internally threaded region 174 that engages a mating externally threaded lower wall section 176 depending downwardly from the collapsible wall 160 and extending radially outward of a valve seat 162 of the drip chamber 132 as illustrated. The valve seat 162 tapers inwardly to an axially-extending opening 164 at a lowermost end 166 of the drip chamber 132.

The threads of the lower internally threaded region 174 and of the externally threaded lower wall section 176 may be of a second pitch, greater than the first pitch of the upper internally threaded region 178 and the upper externally threaded region 180. Although the driver 134 of this second embodiment will move axially relative to the drip chamber 132, as a result of the difference between the first pitch and the second pitch, upon rotation of the driver 134, the engagement of the lower internally threaded region 174 with the externally threaded lower wall section 176 will cause greater relative axial movement of the collapsible wall 160, thereby causing the valve seat 162 to move closer to or further from a valve surface 144 of the valve member 136, depending on the direction of rotation of the driver 134. The flow rate of fluid from the drip chamber 132 is therefore controllable, as in the first embodiment, by rotation of the driver 134 relative to the drip chamber 132. The displacement of the valve seat 162 upon rotation of the driver 134 a given amount is a function of the pitch of the threads of the lower internally threaded region 174 of the driver 134 and the externally threaded lower wall section 176 of the drip chamber 132, but also depends upon the difference between the first and second pitch.

As illustrated in FIGS. 9A, 9B, 10 and 11, the first pitch and second pitch, while different in magnitude, are in the same helical direction. Alternately or in addition to being of different magnitude, the first and second pitch may be in different helical directions from one another.

It will also be recognized that while pairs of continuous threads are provided on the drip chamber 32, 132 and the driver 34, 134, this need not be the case according to every embodiment of the present disclosure. Instead, a discontinuous thread may be used for one of the mating threads, or a tab or shoe may be provided on one of the drip chamber 32, 132 and the driver 34, 134, while the other of the drip chamber 32, 132 and the driver 34, 134 has a groove or race in which the tab or shoe is disposed. According to such an embodiment, the rotation motion of the driver 34, 134 may be transformed into an axial motion of the collapsible wall and associated valve seat. While an embodiment that transmits an axial motion of the driver 34, 134 into an axial motion of the collapsible wall and valve seat would also fall within the scope of the present disclosure, the illustrated embodiments that rely upon conversion of rotational motion (or mixed rotational and axial motion) into axial motion of the collapsible wall and valve seat have certain advantages in that they permit a large rotational movement to be correlated with relatively smaller axial movement, facilitating ease of use.

It should be noted that a number of benefits may follow from the use of the drip chambers 32, 132, although all of these benefits may not be present in all embodiments. For example, because the flow control system illustrated herein does not rely upon a roller clamp for control of the flow through the system, the limitations placed on the tubing material selection are reduced, if not eliminated. As a consequence, a flow control system according to the present disclosure may work well with non-PVC tubing as with PVC tubing. Moreover, because the effects of stress and creep are limited or eliminated over the life of the flow control system when viewed relative to conventional tubing-and-roller-clamp systems, the flow control system according to the present disclosure may be easier to use to maintain a desired flow rate, and may provide better and more reliable resolution than conventional systems.

It will also be recognized that a number of variants have thus been described whereby a higher degree of resolution and a more predictable form of fluid control may be provided than exists relative to conventional systems, such provided by tubing-and-roller clamp systems for example. However, it has also been determined that by providing a groove in the valve surface, even greater flow control may be achieved. In fact, by varying the geometry of the groove, it may be possible to vary the rate of increase of the flow rate through the drip chamber 32 relative to a given rotation of the driver 34 in a controlled fashion. For example, according to the present disclosure, it may be possible to provide one valve surface with a groove that permits large (or coarse) incremental changes in flow rate for a small (or minor) rotation (i.e., a low degree of resolution), while another surface may include a groove that provides very small (or fine) incremental changes in flow rate for relatively large (or major) rotation of the driver 34 (i.e., a high degree of resolution). For delivery of drugs and other fluids to patients requiring tight tolerances on low volumes of fluids, such as neonatal patients, a high degree of resolution in the flow adjustment may be beneficial. For other applications, a low degree of resolution may be permissible.

It will be recognized that the aspects of the present disclosure relating to the drip chamber 32, 132 with rotating driver 34, 134 may be used in conjunction with valve member and valve seat that do not incorporate the additional improvements relating to the grooved surface. Likewise, it may be possible to incorporate the changes described below as to the grooved surface into any of the variants of the fluid control system described above, or in other systems not illustrated or described above. Consequently, the two aspects may be combined, but shall not be required to be combined, according to the present disclosure.

Turning now to FIGS. 12-15, a variety of geometries of grooves are illustrated that may be imparted to a generally cylindrical valve surface of the valve member that is disposed in a drip chamber of the present disclosure. Such grooves may provide enhanced flow control, with each groove geometry resulting in a different flow path profile, with the profiles of various groove geometries disclosed herein compared graphically in FIG. 16. It should be noted that the embodiments according to FIGS. 12-15 are configured to be mated with an valve seat that is also substantially cylindrical. As such, as the valve member and valve seat move relative to each other, at least a portion of the valve member and valve seat remain in sealing engagement, such that the fluid flow past the valve member and the valve seat is through the passageway formed between the groove and the valve seat. It also be recognized that the valve seat need not be generally cylindrical according to all embodiments of the present disclosure, but may in fact be conical shape so as to mate a conical shape valve member.

Figure 12:
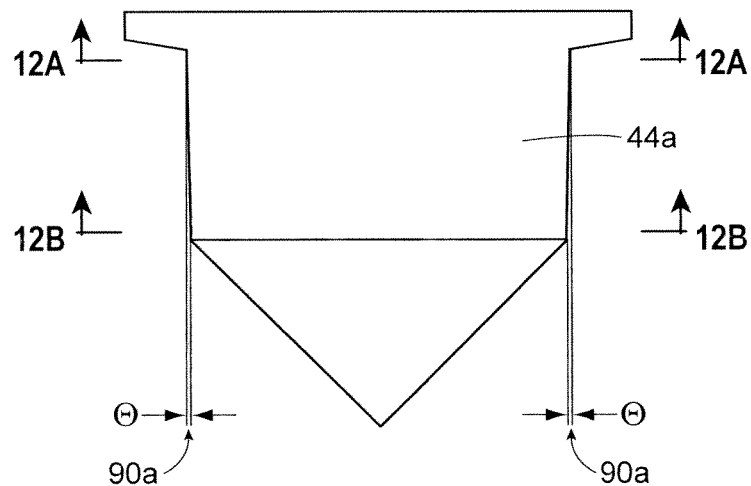
FIG. 12 is a front plan view of a generally cylindrical valve surface of a valve member for use in a drip chamber of the present disclosure including groove in the form of a taper about the circumferential perimeter of the generally cylindrical valve surface.
Figure 12A:
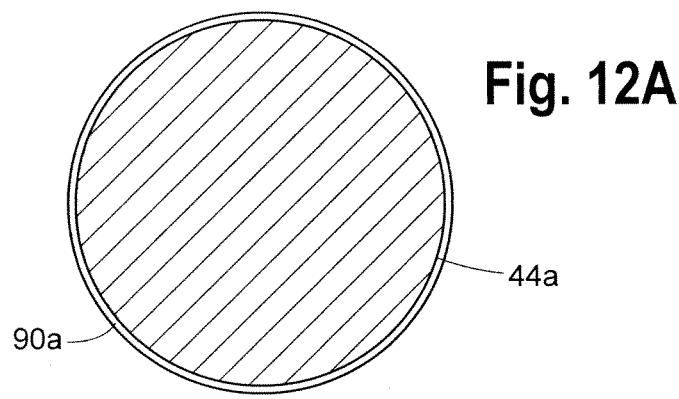
FIG. 12A is a cross-sectional view taken along lines 12A-12A of FIG. 12.
Figure 12B:
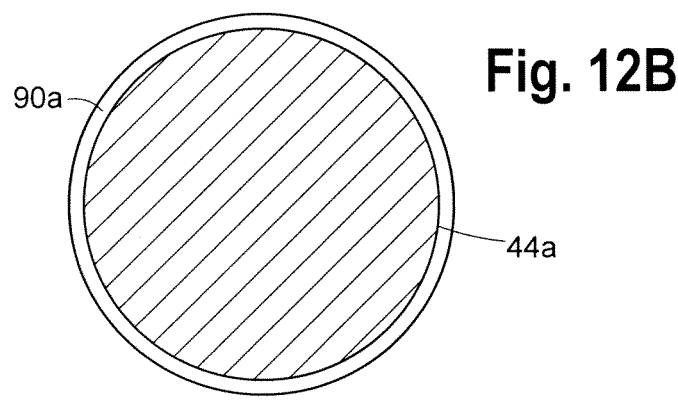
FIG. 12B is a cross-sectional view taken along lines 12B-12B of FIG. 12.
Figure 16:
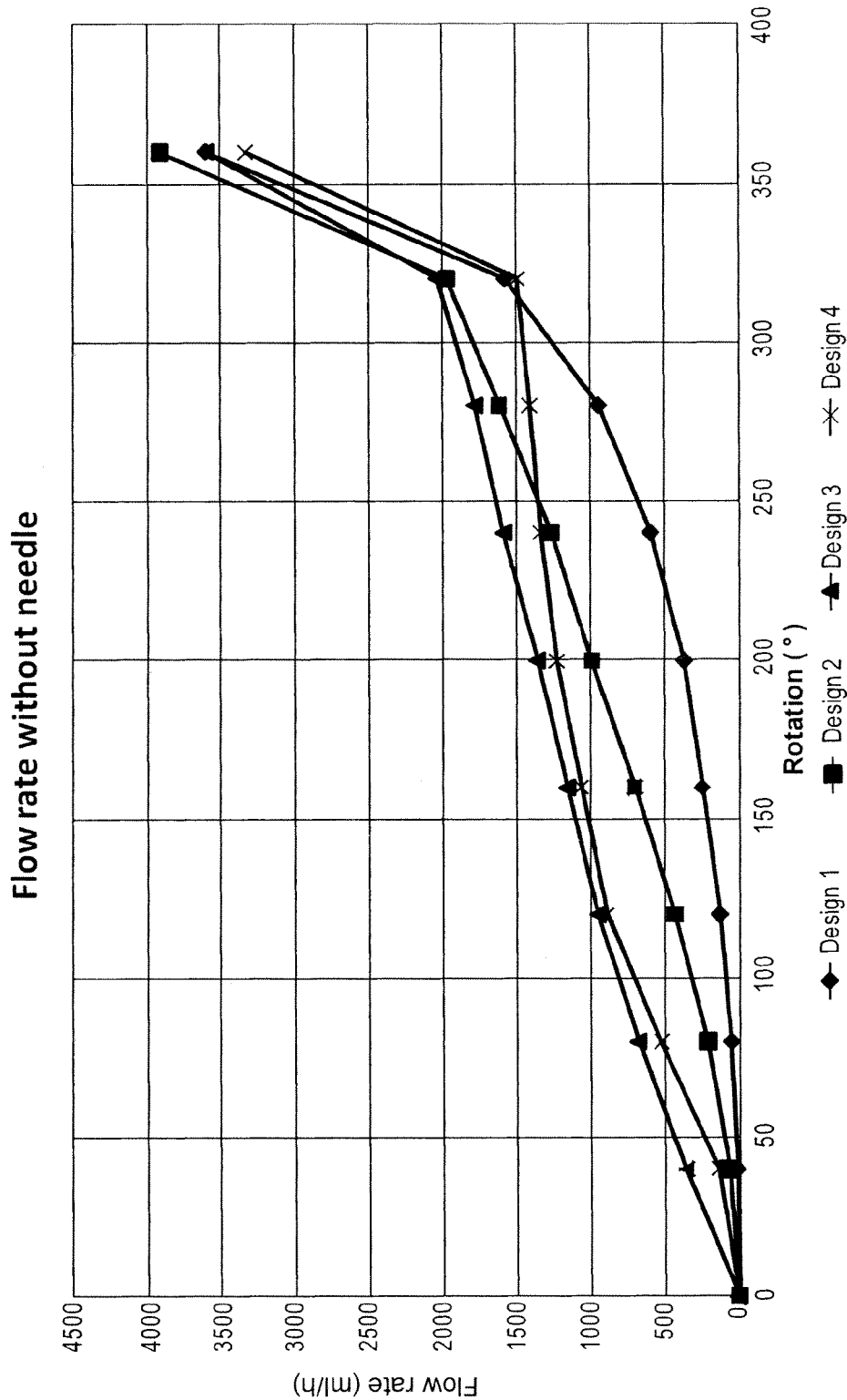
FIG. 16 is a comparative graph illustrating exemplary flow rate profiles of drip chambers of the present disclosure employing the various generally cylindrical valve surface groove geometries for the conical-shaped needles of FIGS. 12-12B ("Design 1"), 13A-13D ("Design 2"), 14A-14E ("Design 3"), and 15A-15D ("Design 4"), charting flow rate (in units of ml/h) along the ordinate, versus rotation of the driver (in units of degrees) along the abscissa.

A first groove 90a is illustrated in FIGS. 12, 12A and 12B, and a generally cylindrical valve surface 44a having this groove geometry is designated as "Design 1" in the graph of FIG. 16. In this embodiment, the generally cylindrical valve surface 44a is provided with an inwardly directed taper of a constant angle, Θ. In an embodiment, the angle Θ is 1°, but it is recognized that other angles are possible, and that the angle need not be constant along the entirety of the valve surface 44a. At the top of the generally cylindrical valve surface 44a, the outer diameter of the mating surface of the generally cylindrical valve surface 44a is equal to the inner diameter of the valve seat of the drip chamber (not shown in FIG. 12). Due to the inwardly directed taper of angle Θ, the outer diameter at the bottom of the generally cylindrical valve surface 44a is less than the inner diameter of the valve seat of the drip chamber. Thus, as illustrated in the cross-sectional views of FIGS. 12A and 12B, a gap between the inner diameter of the valve seat and the generally cylindrical valve surface 44a gets larger with increasing distance from the top of the generally cylindrical valve surface 44a.

A groove 90b in the form of an angled planar cut in an otherwise generally cylindrical valve surface 44b is illustrated in FIGS. 13A-13D. The groove 90b takes the form of a parabolic curve. A generally cylindrical valve surface 44b having this groove geometry is designated as "Design 2" in the graph of FIG. 16. As illustrated in the cross-sectional views of FIGS. 13C and 13D, a gap between the mating surface of the generally cylindrical valve surface 44b along the groove 90b and the valve seat is relatively small at the top of the generally cylindrical valve surface 44b, but relatively large at the bottom of the generally cylindrical valve surface 44b.

A groove 90c having a more complex geometry, in the form of a double parabolic curve, is illustrated in FIGS. 14A-14E. A generally cylindrical valve surface 44c having a groove 90c of this double parabolic geometry is designated as "Design 3" in the graph of FIG. 16. The maximum distance D separating the surface of the groove 90c of FIGS. 14A-14D from the valve seat (not shown) at any distance x down from the top of the generally cylindrical valve surface 44c may be determined according to the following equation:

$$D = \left(\frac{Dmax}{\sqrt{H}}\right) * \sqrt{x}$$

At the top of the generally cylindrical valve surface 44c, D is zero. At the bottom of the generally cylindrical valve surface 44c, D=Dmax. H is the overall height of the generally cylindrical valve surface 44c. As illustrated in the cross-sectional views of FIGS. 14C-14E, the distance D is greater with increasing distance x down from the top of the generally cylindrical region 44c.

Figure 15A:
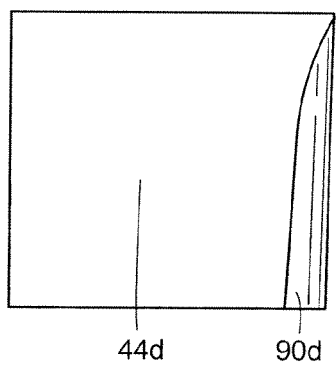
FIG. 15A is a front plan view of a generally cylindrical valve surface of a valve member for use in a drip chamber of the present disclosure, including an rotated arcuate channel along one side of the generally cylindrical valve surface.
Figure 15B:
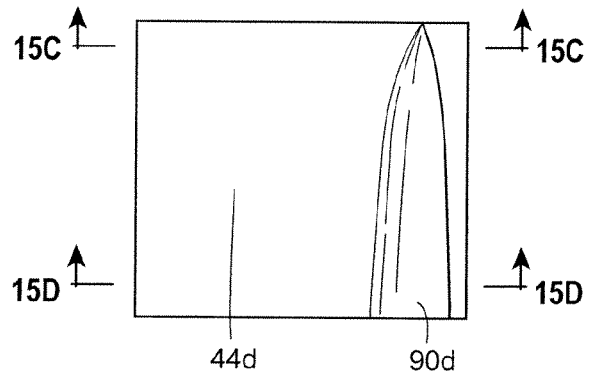
FIG. 15B is a side plan view of the generally cylindrical valve surface of the valve member illustrated in FIG. 15A.
Figure 15C:
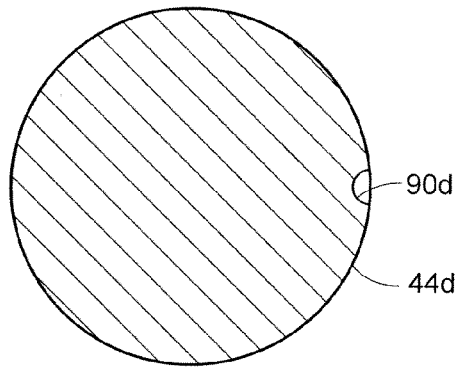
FIG. 15C is a cross-sectional view taken along lines 15C-15C of FIG. 15B.
Figure 15D:
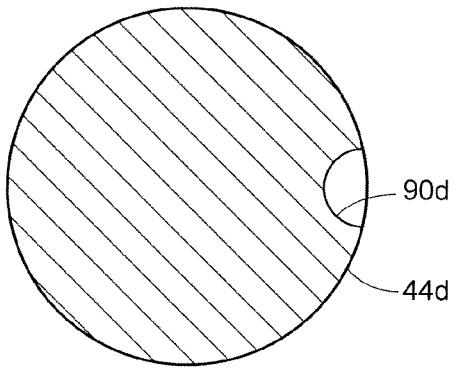
FIG. 15D is a cross-sectional view taken along lines 15D-15D of FIG. 15B.

A generally cylindrical valve surface 44d having a groove 90d of yet a different geometry is illustrated in FIGS. 15A-

15D. A generally cylindrical valve surface 44d having a groove 90d of this geometry is designated "Design 4" in the graph of FIG. 16. The groove 90d is formed of a three-dimensional arcuate cut having a center of curvature coinciding with a vertical axis through a point along the outer perimeter at the top of the generally cylindrical valve surface 44d. As illustrated in the cross-sectional views of FIGS. 15C and 15D, the cross-sectional area of the groove 90d is greater with increasing distance down from the top of the generally cylindrical valve surface 44d.

As mentioned above, FIG. 16 compares the flow rates possible for various changes in the rotational angle of the driver 34, 134, with flow rate (ml/h) along the ordinate and angle of rotation (degrees) along the abscissa. As noted above, Design 1 corresponds to the groove geometry illustrated in FIGS. 12-12B, Design 2 that of FIGS. 13A-13D, Design 3 that of FIGS. 14A-14E, and Design 4 that of FIGS. 15A-15D. It will be recognized that the operation of Design 1 provides a relatively shallow curve, where large changes in angle of rotation correspond to small changes in flow rate, with an steeper increase in flow rate for a given angle of rotation after 200 degrees of rotation. By contrast, Design 4, provides a steeper rise over the first 200 degrees of rotation, but then levels off to a nearly flat profile until approximately 330 degrees of rotation is reached. Designs 2 and 3 show relatively constant increases in flow rate for an incremental change in rotation, although the onset of a constant relationship appears slightly delayed for Design 2 relative to Design 3.

Each of these particular Designs may thus be better suited for particular therapies than others. For example, Design 1 may be better suited for an application where a wide range of particularly low flow rates are desired, such as for an infant for example, but the option for a narrow range of particularly high flow rates is also desirable. Design 3 (or Design 2) may be well suited for applications where a relatively constant relationship between flow rate and angle of rotation is desired, but even small variations in angle provide relatively significant changes in flow rate. Design 4 may be better for a relatively wide range of variation between an extremely low flow rate and an extremely high flow rate, in essence providing for a three-state valve—off, partial function, and full on.

Figure 17:
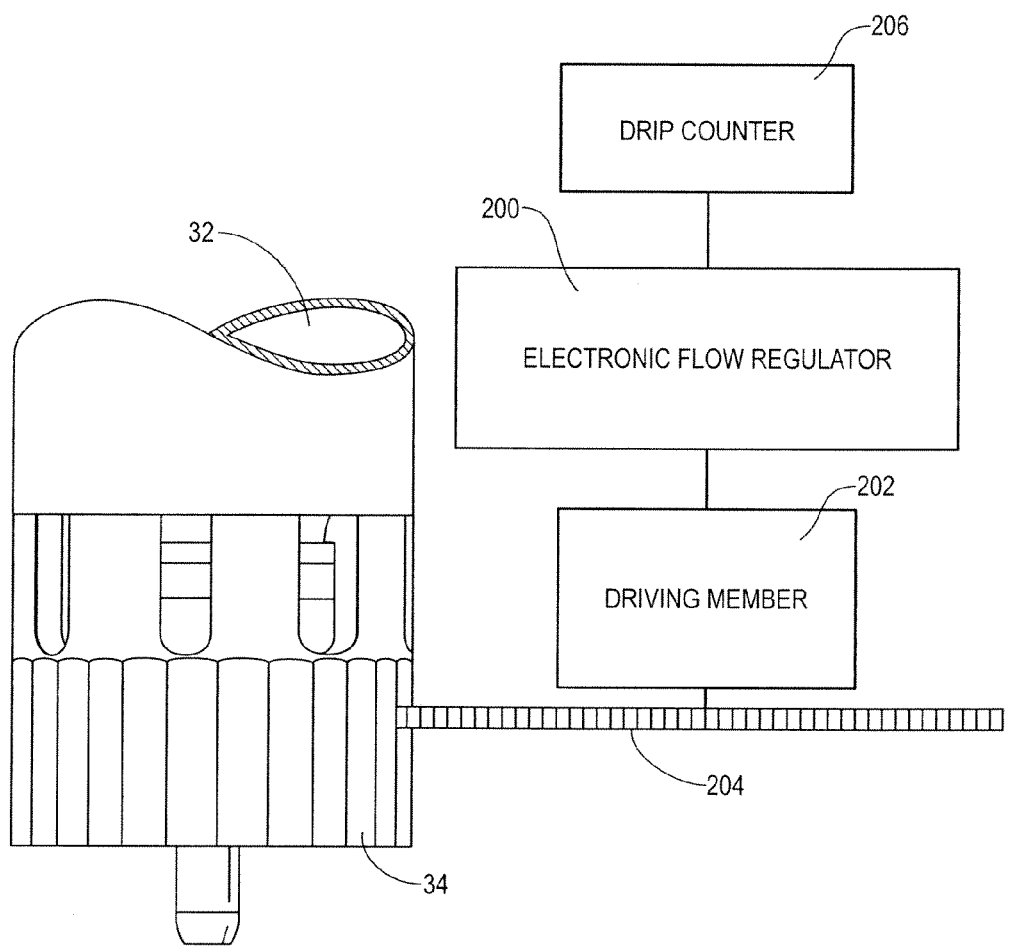
FIG. 17 is a schematic diagram of a system for electronically regulating a flow control system of the present disclosure.

It is recognized that rotation of the driver 34, 134 may be imparted manually or mechanically. For example, as illustrated schematically in FIG. 17, an electronic flow regulator 200 in the form of a controller provided with a keypad and a microprocessor or microcontroller that detects the position of the driver may be in communication with a driving member 202, such as a motor, that drives a gear member 204, such as a circular toothed gear, which automatically rotates the driver 34 relative to the drip chamber 32 (i.e., without direct user input to the driver 34). The microprocessor may be preprogrammed with the calibration of the driver 34 with the valve seat 62 of the associated drip chamber 32, such that by controlling the revolutions in a first direction or in a second direction of a shaft provided on the driving member 202, the microprocessor can signal the driving member 202 to rotate the driver 34 in order to adjust the position of the valve seat 62, thereby adjusting the rate of flow of fluid between the valve member 36 and the valve seat 62. As it is desirable to provide closed loop regulation, a drip counter 206 as is conventionally known to count the drops in the drip chamber 32 may be coupled to the electronic flow regulator 200 and placed in communication with the drip chamber 32. The regulator 200 may thus automatically rotate the driver 34 according to the drops counted by the drip counter 206 in communication with the drip chamber 32. In other embodiments the output of patient monitors or other devices may be utilized to provide the input for closed loop regulation.

The shape of at least one of the valve member 36, 136, or the valve seat 62, 162 may be varied depending on the viscosity of the fluid to be dispensed.

Having described various embodiments of a flow control system, it will be understood that modifications may be made thereto that are still within the scope of the appended claims.

What is claimed is:

1. A flow control system comprising:
a drip chamber having a lower wall section, an upper wall section and a collapsible wall extending between the lower wall section and the upper wall section;
a downwardly depending valve seat attached to the lower wall section, the drip chamber forming a downstream opening in fluid communication with the valve seat;
a valve member disposed in the drip chamber and attached to the upper wall section and having a valve surface engageable with the valve seat; and
a driver rotatably engaged to each of the upper wall section and the lower wall section;
wherein upon rotation of the driver in a first direction, the collapsible wall of the drip chamber moves axially between a collapsed condition in which the valve seat is sealingly engaged with the valve surface and an extended condition in which the valve seat is sufficiently spaced from the valve surface to form a fluid passageway between the valve surface and the valve seat and permit flow through the opening of the drip chamber.

2. The flow control system of claim 1 wherein the rotatable engagement of the driver includes threadable engagement to at least one of the upper wall section and lower wall section.

3. The flow control system of claim 1 wherein the valve surface and valve seat are generally cylindrical.

4. The flow control system of claim 1 further including a groove provided in the valve surface, the groove forming at least a portion of the fluid passageway.

5. The flow control system of claim 4 wherein the groove includes at least one of the form of (a) an inwardly-directed taper about a perimeter of the valve surface, (b) an angled planar cut along at least a portion of the valve surface mating with the valve seat, (c) a double parabolic shape, where a maximum distance D separating a surface of the groove from the valve seat at any distance x down from a top of the valve surface is determined according to the equation $$D = \left(\frac{Dmax}{\sqrt{H}}\right) * \sqrt{x},$$

wherein at a top of the valve surface, D=0, at a bottom of the valve surface D=Dmax, and H is an overall height of the valve surface, and (d) a three-dimensional arcuate cut having a center of curvature coinciding with a vertical axis through a point along a perimeter of the valve surface.

6. The flow control system of claim 4 wherein the valve seat and valve surface are relatively axially displaced by rotation of the driver, the dimensions of the passageway formed by the groove and the valve seat being varied by such axial displacement.

7. The flow control system of claim 4 wherein at least a portion of the valve seat and valve surface remains in sealing engagement as fluid flows through the fluid passageway formed between the groove and the valve seat.

8. The flow control system of claim 4 wherein the valve seat and the valve surface other than the groove remain in sealing engagement to permit fluid flow only through the fluid passageway formed between the groove and the valve seat.

9. The flow control system of claim 1 wherein the valve seat is integrally attached to the lower wall section.

10. A method for regulating the flow of fluid through a drip chamber, comprising:
rotating a driver that is in rotatable engagement with an upper wall section and a lower wall section of a drip chamber relative to the drip chamber to axially move a collapsible wall that extends between the upper and lower wall sections between a collapsed condition in which an associated valve seat is sealingly engaged with a valve surface and an extended condition in which the valve seat sufficiently spaced from the valve surface to form a flow passageway between the valve surface and the valve seat to permit flow therethrough.

11. The method of claim 10, wherein the driver rotates relative to the upper wall section without relative axial movement between the driver and the upper wall section, and rotates relative to the lower wall section with relative axial movement between the driver and the lower wall section.

12. The method of claim 10, wherein the driver rotates relative to the upper wall section with relative axial movement between the driver and the upper wall section, and rotates relative to the lower wall section with relative axial movement between the driver and the lower wall section.

13. The method of claim 10, wherein the valve surface has a groove therein, and in the extended condition the valve seat is sufficiently spaced from the valve surface to form a flow passageway defined by the groove and the valve seat to permit flow only through the groove.

14. The method of claim 10, wherein the driver is rotated automatically relative to the drip chamber.

15. The method of claim 14, further comprising counting drops in the drip chamber and automatically rotating the driver according to the drops counted.

* * * * *